United States Patent [19]

Partenheimer

[11] 4,094,816

[45] * June 13, 1978

[54] METHOD FOR STABILIZING A PHOSPHORUS-VANADIUM-OXYGEN COMPLEX CATALYST

[75] Inventor: Walter Partenheimer, Naperville, Ill.

[73] Assignee: Standard Oil Company, Chicago, Ill.

[ * ] Notice: The portion of the term of this patent subsequent to Apr. 26, 1994, has been disclaimed.

[21] Appl. No.: 753,551

[22] Filed: Dec. 22, 1976

Related U.S. Application Data

[63] Continuation-in-part of Ser. No. 616,370, Sep. 24, 1975, Pat. No. 4,020,174.

[51] Int. Cl.² .................. B01J 23/92; B01J 27/28
[52] U.S. Cl. ...................... 252/415; 260/346.75; 260/533 R; 260/533 N
[58] Field of Search ............... 252/413, 414, 415, 411; 260/346.8 A, 346.75

[56] References Cited

U.S. PATENT DOCUMENTS 4,020,174  4/1977  Partenheimer ............ 260/346.8 A

Primary Examiner—Henry R. Jiles
Attorney, Agent, or Firm—Stephen L. Hensley; Arthur G. Gilkes; William T. McClain

[57] ABSTRACT

The present disclosure relates to a method for the stabilization of certain phosphorus-vanadium-oxygen complex catalysts by the repetitive reactivation of such catalysts using a specified class of reactivating agents. The present method is specifically applicable to the stabilization of phosphorus-vanadium-oxygen complex catalysts which are suitable for the production of maleic anhydride from aromatic or aliphatic feed streams. In a specific instance, the stabilization process incorporates passing a feed stream of an aliphatic hydrocarbon and oxygen over a phosphorus-vanadium-oxygen catalyst to cause it to deactivate, thereafter contacting the deactivated catalyst with a specified class of reactivating agents and thereafter repeating this sequence at least once. This process tempers the catalyst so it deactivates at a lower rate and is improved in its performance.

27 Claims, No Drawings

METHOD FOR STABILIZING A PHOSPHORUS-VANADIUM-OXYGEN COMPLEX CATALYST

RELATED APPLICATIONS

This application is a continuation-in-part of my recently allowed copending application U.S. Ser. No. 616,370, filed Sept. 24, 1975, now U.S. Pat. No. 4,020,174. Said application and its teachings are incorporated into this specification by specific reference thereto.

BACKGROUND OF THE INVENTION

1. Field of the Invention

The field of art to which this invention pertains is stabilization of phosphorus-vanadium-oxygen complex catalysts and in particular, the stabilization of catalysts used for the production of oxygenated products including aldehydes, ketones, acids, anhydrides, and mixtures thereof from hydrocarbon feedstocks. In a specified instance, the claimed stabilization procedure can be used on a catalyst used for the production of maleic anhydride from a specified feedstock, namely, normal butane in air. Pertinent U.S. Patent and Trademark Office classifications include Class 260, subclass 346.8.

2. Description of the Prior Art

Relevant prior art includes U.S. Pat. No. 2,773,921, issued December 11, 1956, having inventors Paul N. Rylander, Jr., and Wilford J. Zimmerschied. This patent was officially classified in Class 260–683.15, and generally relates to a phosphoric acid-vanadium-pentoxide catalyst and a hydrocarbon conversion process using the catalyst.

U.S. Pat. No. 3,915,892, issued Oct. 28, 1975, also may be considered as relevant prior art. This patent teaches a method of production of a mixed vanadium-phosphorus oxide catalyst which includes a specified procedure for dehydrating the catalyst and activating it for use in an oxidation process.

Great Britain Pat. Specification No. 1,291,354, published Oct. 4, 1972, relates to a method for the production of maleic anhydride using a phosphorus-vanadium-oxygen complex catalyst. A volatile inorganic phosphorus compound is added to a feed mixture of $C_4$ hydrocarbons which is passed over the catalyst.

Of general interest, especially for its teaching of the specific catalyst which can be used herein, is U.S. Pat. No. 3,862,146, issued Jan. 21, 1975, having Edward M. Boghosian as its inventor. This patent teaches the oxidation of butane to maleic anhydride in the presence of phosphorus-vanadium-oxygen complex catalysts containing activators from the group of zinc, bismuth, copper, or lithium or mixtures thereof.

The presently claimed method for stabilization of phosphorusvanadium-oxygen complex catalyst is especially valuable in that a produced catalyst can quickly be broken in for use in a commercial reactor by practice of the claimed sequence of deactivation followed by reactivation. Specifically the catalyst can be contacted with a deactivating atmosphere (generally a hydrocarbon in air and preferably at a relatively high temperature) to deactivate the catalyst. Thereafter the catalyst can be contacted at reactivating conditions with an effective amount of a reactivating agent selected from a specified class of materials, the above steps are then repeated at least once. By alternately deactivating and reactivating the catalyst it eventually reaches a condition where it becomes less susceptible to deactivation.

The presently claimed stabilization method can be utilized as the final step of a catalyst preparation procedure providing a prestabilized catalyst which is ready for process use.

This stabilization procedure works for an obvious advantage in the commercial environment, since the commercial reactor will not have to be used to stabilize the catalyst.

SUMMARY OF THE INVENTION

The present invention can be summarized as a process for stabilizing a phosphorus-vanadium-oxygen catalyst which comprises a sequence of steps including contacting said catalyst with a gaseous mixture containing molecular oxygen, preferably with a gaseous mixture containing molecular oxygen and a hydrocarbon having less than about 10 carbon atoms per molecule, for a period of time to deactivate the catalyst, thereafter contacting said catalyst with a reactivating material selected from a specified class of materials and repeating the above sequence of steps at least once. This procedure conditions the catalyst so that when it is placed in service for the production of desired oxygenated produces from hydrocarbons it is less susceptible to catalyst deactivation.

A broad embodiment of this invention resides in a method for stabilizing a phosphorus-vanadium-oxygen-complex catalyst having an atomic ratio of phosphorus to vanadium in the range of from about 0.5 to about 5, which method comprises: (A) contacting said catalyst at a temperature in the range of from about 350° to about 600° C. with a gaseous mixture containing molecular oxygen for a period of time sufficient to deactivate the catalyst; (B) contacting said catalyst with an effective amount of a reactivating material selected from the group consisting of: (1) molecular chlorine or fluorine, or mixtures thereof; (2) halides of fluorine, chlorine, bromine, or iodine, being in the vapor state above 250° C. at atmospheric pressure represented by the following formula $C(X)_n$, where each X is a selected halide and $n$ is an integer from about 1 to 4, any remaining radicals being hydrogen or mixtures thereof, (3) organic halides of fluorine, chlorine, bromine or iodine being in the vapor state above about 250° C. at atmospheric pressure represented by the formula $R(X_1)_m$, where R is alkane, alkene or alkyne, of straight or branched structure, having at least two carbon atoms and $X_1$ is independently a primary, secondary, or tertiary halide and $m$ is an integer of from 1 to about 20 consistent with the number of carbon atoms of said structure, or mixtures thereof; (4) Hydrogen halides or mixtures thereof at reactivating conditions including a temperature in the range of from about 300° to about 500° C., and repeating the sequence of steps (A) and (B) above at least once.

In another embodiment, this invention resides in the stabilization process as described above including in step (A) of contacting said catalyst with gas containing molecular oxygen and a hydrocarbon having less than about 10 carbon atoms per molecule.

In a more limited aspect another embodiment of my invention resides in a method for stabilizing a phosphorus-vanadium-oxygen complex catalyst having an atomic ratio of phosphorus to vanadium in the range of from about 0.5 to 5 which method comprises: (A) contacting said catalyst at deactivation conditions including a temperature above about 350° C with a gas containing molecular oxygen and butane for greater than about one hour; (B) contacting said catalyst with an effective amount of carbon tetrachloride at reactivation conditions including a temperature in the range of from about 300°–500° C.; and repeating the sequence of steps (A) and (B) above at least once.

DETAILED DESCRIPTION OF THE INVENTION

The present stabilization method can take place on many phosphorusvanadium-oxygen complex catalysts. In some instances, these catalysts contain phosphorus, vanadium, and oxygen, but other materials such as Group IA or IB metals for activation or stabilization of the catalyst may be used.

Specific catalysts which can be utilized to produce maleic anhydride from butane or atomatic materials or mixtures thereof are described in U.S. Pat. No. 3,862,146. Such patent has as its inventor Edward M. Boghosian, and is assigned to Standard Oil Company (Indiana). The above patent is hereby incorporated into this specification by specific reference thereto.

The invention of U.S. Pat. No. 3,862,146 described above can be summarized as an oxidation process using a phosphorus-vanadium-oxygen complex metal promoted catalyst for the production of oxygenated products and in particular maleic anhydride.

The above cited patent can be abstracted as follows:

The oxidation of butane to maleic anhydride in the presence of a phosphorus-vanadium-oxygen complex catalyst is enhanced by the addition to the catalyst of a zinc, bismuth, copper or lithium metal activator. The yield of the oxidation may be increased by as much as 50% without any loss in selectivity to the production of maleic anhydride.

The broadest claim of said referenced U.S. Patent is included below:

A process for the preparation of maleic anhydride which comprises: contacting a feedstock consisting essentially of 50% at least N-butane and a gas-containing molecular oxygen in the vapor phase with a catalyst complex consisting essentially of phosphorus-vanadium-oxygen and a metal activator selected from zinc, copper, bismuth, lithium or mixtures of these, said catalyst complex comprising from about 0.5 to 5 atoms of phosphorus for each atom of vanadium and from 0.05 to 0.5 atoms of said metal activator for each atom of vanadium.

While the above reference patent does specifically describe a certain process and catalyst using such process, the present disclosure is not limited to those stated limitations.

Other patents which teach and describe various phosphorus-vanadium-oxygen complex catalysts include the above-cited U.S. Pat. Nos. 3,915,892, 3,156,705, 3,156,706, 3,156,707, 3,238,254, 3,255,211, 3,255,212, 3,255,213, 3,288,721, 3,293,268, and 3,625,863, all of which contain general teachings as to methods of catalyst manufacture, catalytic composition and processing use of many phosphorus-vanadium-oxygen complex catalysts. The above patents are specifically incorporated into this application by specific reference thereto.

The specific oxygenated product will depend on reaction conditions, feedstock selection and catalyst type utilized. Hydrocarbon feedstocks and the products produced therefrom include: ethane and products which are produced from it generally of non-acidic materials; propane which can produce acrylic acid, acetic acid, maleic acid, and in some instance, propionic acid; normal butane, butenes or butadienes which can produce in certain instances, maleic anhydride and other products including acetic acid, acrylic acid, and methyl acrylic acids; normal pentane, which can produce maleic anhydride and other materials including formic acid and other trace materials; propylene which can be used to produce maleic anhydride and other acid products, paraxylene, which can be used to produce maleic anhydride; orthoxylene, which can be used to produce phthalic anhydride and, in some cases, maleic anhydride; benzene, which can produce in many instances, high concentrations of maleic anhydride and other acetic based materials.

The catalysts contemplated for use in the claimed stabilization process are generally made from the reaction of vanadium pentoxide and phosphoric acid under controlled conditions. Other vanadium and phosphorus containing materials can be used in the catalyst preparation. Activators such as zinc, lithium, copper, bismuth or group IA and IIA metals for catalyst stabilization may also be used. Depending on the feed to be processed and the desired products the composition of the catalyst can be varied significantly.

For maleic anhydride production from normal butane or butenes a suitable catalyst has an atomic ratio of phosphorus to vanadium of from about 0.5 to about 5. An even more preferred ratio is a value of from around 1.0 to about 1.6. Other metals may be incorporated into the basic catalyst in varying ratios of from about 0.05 to about 5 atoms of activator for each atom of vanadium. An especially useful catalyst for maleic anhydride production from normal butane has an atomic ratio of phosphorus to vanadium to zinc of about 1.15:1.0:0.19.

In order to stabilize the catalyst as claimed herein, it is necessary to subject it to a series of deactivation steps followed by reactivation steps. Specifically, the deactivation step will occur under what are referred to as a deactivating conditions including an atmosphere of molecular oxygen or an atmosphere of molecular oxygen in combination with a selected hydrocarbon. Specifically, when using oxygen in the absence of hydrocarbons, air is a suitable candidate for deactivation. When using molecular oxygen and a hydrocarbon, many hydrocarbons can be selected. It is preferred that the hydrocarbon be selected which will not lay down appreciable coke on the catalyst. The concentration of hydrocarbon in the molecular oxygen stream should be selected so that the mixture is outside of the explosive range (either above or below the explosive envelope). In a preferred sense, the hydrocarbon should be a relatively light one including materials such as methane, ethylene, or ethane, propane, or propylene, normal or isobutanes or normal or isobutylenes or hydrocarbons having less than about 10 carbon atoms per molecule. Additional hydrocarbons which can be used include aromatics such as xylenes or benzene. In many instances, the deactivation procedure will itself produce valuable products. If normal butane or butenes are utilized to deactivate the catalyst in an atmosphere of air, maleic anhydride can be produced as a primary reaction product. This contemplates that in some instances the deactivation conditions will include operations which will produce valuable products.

The time necessary for the deactivation of the catalyst to take place will vary depending upon the temperature and the specific deactivation conditions utilized. for instance, when relatively high temperatures are utilized, deactivation will take place more rapidly. In some instances this may be a preferable method of forcing the catalyst to become deactivated (and thereafter reactivated) and is especially suitable when the claimed stabilizing process is used as a finishing step in a catalyst production procedure. In such cases the catalyst can be subjected to accelerated deactivation followed by reactivation prior to loading it into the commercial reactor resulting in a savings to the chemical producer.

Deactivation conditions include temperatures which can vary depending upon the catalyst's composition and the deactivating atmosphere utilized. Temperatures anywhere from about 400° to about 600° C., can be used with preferred temperatures being in the range of from about 450° to about 550° C. In certain instances, if air is used as the deactivating atmosphere without the presence of a reducing gas, precautions must be taken to prevent the production of $VPO_5$ which may, in some instances, be irreversibly produced thereby permanently deactivating the catalyst. For this reason, it is generally preferred in the deactivating procedure, to operate at as high a temperature as possible consistent with minimal $VPO_5$ formation.

When using a deactivating atmosphere of a hydrocarbon and air, the concentration of the hydrocarbon can be varied anywhere outside of the explosive envelope of the resultant air-hydrocarbon mixture. In instances where butane is used in the deactivating atmosphere, butane concentrations of anywhere from less than 1 to about 1.7 volume percent butane in air can be used to deactivate the catalyst. When such deactivating atmospheres are utilized, a generally good deactivation temperature is anywhere from around 450° to about 520° C. with the higher temperature generally being preferred in order to enhance the rate of deactivation of the catalyst.

The time necessary for deactivation of the catalyst as mentioned above will vary, depending upon the specific deactivating atmosphere utilized and the temperature at which such deactivating atmosphere contacts the catalyst. Also, the previous history of the catalyst, whether it has been used for other processing or itself is a spent catalyst ready for reuse in a process, will also affect its rate of deactivation. The time period can vary anywhere from less than an hour to many hours or days, again depending on the deactivation conditions.

When contacting the catalyst with a deactivating atmosphere at conditions sufficient to cause deactivation the catalyst will lose its selectivity for producing a desired oxygenated product reducing the yield of such product from the process. In many instances, this will be accompanied by an increase in conversion of the feed, but not necessarily to desirable products. The extent of deactivation will vary and it is necessary, depending on the specific catalyst formulation and deactivating atmosphere and conditions utilized, to judge from previous experience the deactivation necessary before reactivation should take place to effect the claimed stabilization of the catalyst.

The reactivating step which follows the deactivating step is fully described in my above-cited co-pending application. This step is necessary in order to compensate for the deactivation which has previously taken place on the catalyst. As will be illustrated below, the alternate deactivation and reactivation of the catalyst ultimately produces a catalyst which has an increased ability to withstand catalyst deactivation and additionally improves its selectivity for the production of the desired oxygenated products(s).

The reactivating conditions which are contemplated for use in the stabilization method claimed herein, include the use of an effective amount of a reactivating agent to contact said catalyst and thereby cause at least its selectivity to be increased for the production of desired oxidation product or products.

The concentration of the activating agent passing over the catalyst should be monitored so as to prevent damage to the catalyst from excess additions. Additional problems associated with activating agent additions include the production of corrosive end products which possibly could damage plant equipment.

It has been found in determining what is an effective amount of reactivating agent that there is some minimum concentration of the reactivating agent which should be passed into the reaction zone to effect the increase in selectivity of the catalyst. However, it is difficult to ascertain the concentration as an absolute quantity since reactor designs would have a substantial influence on the actual concentration to which the catalyst within the reaction zone would be exposed. Accordingly then, the better approach would be to state that a minimum total quantity based generally on the phosphorus and/or vanadium content in the reaction zone be passed into the reaction zone for reactivating conditions to give the necessary selectivity increase.

Carrier gases are contemplated when the reactivating procedure occurs to move the reactivating agent through the catalyst bed. The carrier gases are not necessarily critical in their choice and can include materials such as nitrogen, butane, oxygen, or any other available gaseous stream which would be compatible with the reactivating agent and would not degrade the catalyst performance.

It is contemplated that before and/or after passage of reactivating agent through the catalyst bed that a gas purge be used to remove entrained reactivating agent and other materials from the catalyst. Such purge materials can include nitrogen or other inert gases or light hydrocarbons such as butane.

It has been found after the reactivation of the catalyst that a steam treatment will sometimes improve the conversion level of the catalyst. The exact mechanism taking place which allows the steam purge to additionally enhance catalyst performance is not specifically known. Evidence indicates that when using alkyl halides as reactivating agents that at certain temperatures a small amount of carbon residue is laid down on the catalyst which may adversely affect its conversion. Accordingly then, it is theorized that the passage of steam over a catalyst in the absence of the reactivating agent will cause a water gas reaction to take place effectively removing the deposited carbon from the catalyst and allowing an enhanced weight yield to be obtained.

Reactivation conditions include a temperature in the range generally from about 300° to about 650° C. In a most preferred instance, the reactivating conditions should include a temperature within the range of from about 300° to about 550° and in some instances from about 300° to about 450° C. Of course, the temperatures of reactivation will vary depending on the specific catalyst and oxidation process ultimately utilized. When normal butane and air or enriched oxygen are passed into the reaction zone for the production of maleic anhydride, it has been found that a most preferred reactivating temperature will be somewhere above 300° C.

but below 600° C. when a carbon tetrachloride reactivating agent is used.

For the most successful reactivation of a butane oxidation catalyst for producing maleic anhydride when using a carbon tetrachloride reactivating agent it has been found that reactivation temperatures greater than about 300° C. are desired to cause increases in selectivity but less than about 400° C. are needed to reduce losses in catalyst conversion unless a subsequent steam treatment takes place.

The reactivating agents which may be used in the reactivating procedure claimed herein generally include materials such as molecular halogens or mixtures thereof, or compounds containing one or more halide radicals or mixtures thereof. However, within the broad category of halides there obviously exists materials with hazardous properties, e.g. self-detonation or highly corrosive tendencies which while within the definition of halides for reactivating agents would not necessarily be effective since they destroy the catalyst and/or the processing equipment. Accordingly then in defining the reactivating agents or halides used herein, the inoperative species are to be precluded.

One of the basic requirements when utilizing the halide materials as reactivating agents is that they remain in a vapor phase when employed at reactivating conditions. Accordingly then, materials which have reasonably high boiling points are not practical and would present processing difficulties. It is preferable that the halide materials be in a vapor phase at temperatures above a minimum of about 250° C. at atmospheric pressure. The specific reactivating agents can include pure components or mixtures of components. Specifically useful in the reactivating step herein are the halides including the gaseous forms of fluorine, chlorine, and bromine. In some instances gaseous iodine may be used but its boiling point is sufficiently high so that it may not present a favorable reactivating agent when used at low temperatures. Specific reactivating agents can include but are not necessarily limited to the following: hydrogen chloride, trichloromethane, dichloromethane, monochloromethane, hexachloroethane, halide substituted ethanes, propanes, butanes (normal or iso), pentanes (normal or branched), hexanes (branched or straight), and other chloride or halide containing aliphatics. Other specific halides which can be utilized include materials such as 1,6-dichlorohexane, 1,2-dichlorohexane, 1,2-dibromohexane, 2,2-dichlorohexane, 2,3-dichlorohexane, 2,5-dichlorohexane, and 3,4-dichlorohexane, normal hexylbromide, sec-hexylbromide and 3-bromohexane.

Organic halides of fairly low carbon number (generally 4 or less) are preferred to reduce the possibility of coke formation during reactivation.

Inter halogens which may be utilized include gases which have reasonably low boiling points such as ClF, ClF$_3$, BrF, BrCl, IBr, BrF$_5$, F$_2$O, Cl$_2$O ClO$_2$ (potentially explosive), Cl$_2$O$_6$, Cl$_2$O$_7$, Br$_2$O and oxy acids of chlorine, bromine, and iodine. Other materials which may be utilizable at high reactivation temperatures include products such as CF$_4$, CHF$_3$, Freon 12, Freon 13, Freon 22, Freon 21 and trichloro acetic acid.

One class of reactivating agents includes organic halides being in the vapor state above about 250° C at atmospheric pressure represented by the formula:

$$C(X)_n$$

where each X is a selected halide and $n$ is an integer from 1 to 4, any remaining radicals being hydrogen. Carbon tetrachloride is representative of the group and is especially preferred.

Another class of reactivating agents include organic halides being in vapor state above about 250° C at atmospheric pressure represented by the formula:

$$R(X_1)_m$$

where R is alkane, alkene or alkyne of straight or branched structure having at least two carbon atoms and $X_1$ is independently a primary secondary or tertiary halide and m is an integer of from 1 to about 20 consistent with the number of carbon atoms of said structure.

The number of sequences of deactivating steps followed by reactivating steps which are needed in order to stabilize the catalyst will vary depending upon the catalyst used, the specific feedstock and desired oxygenated products and the degree of deactivation and reactivation which take place in the claimed stabilization process. In many instances, it is required that the catalyst be deactivated and then reactivated at least once in order that a sufficient stabilization take place to justify the use of the claimed invention. In cases where a catalyst is deactivated with butane in air at temperatures of around 520° C. followed by reactivation, as many as seven cycles of the above operations may be needed before the catalyst has become sufficiently stable to withstand processing conditions to take advantage of the claimed stabilization procedure. Of course, the number of cycles of deactivation followed by reactivation can be more and vary up to 20 or more. When the stabilization method as claimed herein is used as an integral part of the catalyst manufacturing step it is, of course, desired to minimize the number of swings between deactivation conditions followed by reactivation conditions in order to make an economical priced catalyst.

A single deactivation followed by a single reactivation in many instances will produce a stabilized catalyst.

The present stabilization method can also take place in a commercial reactor if it is desired to stabilize the loaded catalyst in situ. Under such conditions, it may be desired to start-up the catalyst under normal production operations and produce the desired oxygenated product until an uneconomical deactivation takes place. Then reactivation of the catalyst can take place and thereafter optionally, more severe deactivations can take place to accelerate the rate of deactivation and thereby complete as many deactivation and reactivation cycles as deemed necessary in order to make the catalyst more stable.

It is also possible to start up a catalyst in the reverse sequence of stabilization methods claimed herein, namely, to first reactivate a catalyst which for some reason is deactivated, followed by an operational use of the catalyst and/or a deactivation of the catalyst, such deactivation followed by either operational use of the catalyst or a reactivation procedure. It is important in taking advantage of the stabilization method claimed herein that at least one cycle of deactivation and reactivation takes place on the catalyst.

In order to more adequately understand and describe the various catalytic properties which are effected through the use of the catalyst described and used in this invention, the following definition of terms is presented.

$$\text{Conversion} = \frac{\text{moles hydrocarbon feed consumed}}{\text{moles hydrocarbon charged}}$$

$$\text{Selectivity} = \frac{\text{moles desired oxidation product produced}}{\text{moles hydrocarbon feed consumed}}$$

Mole Yield = (Conversion) (Selectivity)

In a specific instance wherein a feed stream containing essentially normal butane is charged to the reaction zone for the production of maleic anhydride the conversion, selectively and mole yield are shown below.

$$\text{Conversion} = \frac{\text{moles n-}C_4 \text{ consumed}}{\text{moles n-}C_4 \text{ charged}}$$

$$\text{Selectivity} = \frac{\text{moles maleic anhydride produced}}{\text{moles n-}C_4 \text{ consumed}}$$

Mole Yield = (Conversion) (Selectivity)

In instances in which a weight yield is desired for the production of maleic anhydride from normal butane the following calculation can be used.

Weight Yield = (Conversion) (Selectivity) (1.69)

The above conversion, selectivity and yields on the molar basis times 100 equal percentage conversion, selectivity and mole yields. When determining a weight yield it is necessary to know the ratio of the molecular weights of the feed hydrocarbon and the oxygenation product and accordingly, the weight yield for the production of maleic anhydride from normal butane is defined as the product of the molar conversion times the molar selectivity (for normal butane to maleic anhydride) all times 1.69. The theoretical maximum production of maleic anhydride from normal butane would give a weight yield of 1.69 pounds of maleic anhydride for each pound of normal butane consumed assuming 100 percent selectivity and conversion. In stating the weight yield on a percentage basis, it merely reflects the quantity of theoretical weight yield of maleic anhydride times 100. Accordingly then, the theoretical weight percent yield would be 169 percent.

The following examples are presented to specifically illustrate certain embodiments of the claimed stabilization process herein, and are not necessarily presented so as to unduly limit or restrict the scope of the claims.

EXAMPLE I

In this example repetitive regenerations were performed on a phosphorus-vanadium-oxygen catalyst to illustrate a method of conditioning the catalyst. The catalyst had an atomic ratio of P/V of about 1.2 and a zinc activator in an atomic ratio of Zn/V of about 0.2. The vanadium had an average valence around +4.

The apparatus utilized in this Example consisted of a small tubular reactor containing about 4 grams of catalyst. During "Butane Feed and Catalyst Performance" operations a gaseous mixture of normal butane in air contacted the catalyst a weight hourly space velocity of about 1.4 (based on butane) at atmospheric pressure. The normal butane was present as about 1.1 volume percent of the gaseous mixture at the catalyst temperature indicated in Table I. During various segments of catalyst life its temperature was raised to 520° C. and contacted with the butane-air mixture to accelerate deactivation and ultimate tempering of the catalyst.

After each 4 hour contact at about 520° C. the catalyst was allowed to cool to about 450° C. and then allowed to continue the air-butane gaseous contact for about 30 or more hours.

Before the catalyst was contacted with carbon tetrachloride a ½ hour purge with nitrogen took place. The carbon tetrachloride treatment took place at about 450° C. by injecting into a nitrogen steam flowing over the catalyst at about 80 ml/min. about 0.07 ml of carbon tetrachloride (3 weight percent based on the catalyst) over a 15 second time period.

After carbon tetrachloride contact the catalyst was again purged with nitrogen as described above. In some cases a stream of 85 volume percent water in nitrogen was passed over the catalyst at a weight hourly space velocity of about 1.4 for about one hour.

After the optional steam treatment the catalyst was again contacted with the butane-air mixture at about 450° C and the entire sequence repeated as indicated in Table I.

About thirty hours after the high temperature butane-air contact, conversion, selectivity and weight yield determinations of maleic anhydride production were made at the indicated temperatures. The same measurements were made after each carbon tetrachloride and steam treatment.

The information developed indicated that after each successive contact of the catalyst with butane and air at 520° C. the catalyst was reduced in overall effectiveness to a much lower degree. After the fourth contact of the catalyst with carbon tetrachloride a high temperature contact with butane and air reduced the yield of maleic anhydride by only 1 percentage point. This illustrates a method of pretreating or tempering the catalyst so that its rate of selectivity and/or yield declines can be substantially reduced. This results in the production of a catalyst which will deactivate at a slower rate and which would reduce the need for process interruptions to either reactivate the catalyst or load new catalyst into the process reaction zone.

It is also interesting to note that the reduced rate of deactivation of the catalyst after the claimed stabilization process is not the result of the catalyst losing its initial high conversion since after the fifth sequence (599 hours catalyst life) the conversion of the catalyst was about the same as the initial conversion.

The data evidencing the above findings are presented in Table I below. In such Table the indicated operation were performed as follows: "Butane Feed" indicates the above described mixture of 1.1 volume percent normal butane in air; "Catalyst Performance" indicates the onstream measurement of the catalyst's catalytic properties, i.e., conversion, selectivity and weight yield as defined in the specification; "Temperature Runaway" indicates passing the above butane-air mixture over the catalyst but at an increased temperature (generally around 520° C.) to accelerate catalyst deactivation; "Steam Treatment" indicates an operation in which steam is passed over the catalyst to remove coke or other impurities from it; and "$CCl_4$ treatment" indicates a reactivation procedure using carbon tetrachloride as described above.

TABLE I

| Operation | Time On-Stream, Hrs. | Temperature, ° C. | Conversion to MAN, Percent | Selectivity to MAN, Percent | Weight Yield to MAN Percent |
|---|---|---|---|---|---|
| Butane feed | 0–71 | 448 | — | — | — |

TABLE I-continued

| Operation | Time On-Stream, Hrs. | Temperature, °C. | Conversion to MAN, Percent | Selectivity to MAN, Percent | Weight Yield to MAN Percent |
|---|---|---|---|---|---|
| Catalyst Performance | 71 | 448 | 81 | 62 | 85 |
| Temp. Runaway | 71–75 | 522 | — | — | — |
| Butane Feed | 75–107 | 450 | — | — | — |
| Cat. Performance | 107 | 453 | 80 | 47 | 63 |
| Butane Feed | 107–122 | 450 | — | — | — |
| CCl₄ treatment | 122 | 400 | — | — | — |
| Butane Feed | 122–130 | 450 | — | — | — |
| Cat. Performance | 130 | 451 | 60 | 54 | 55 |
| Butane Feed | 130–155 | 453 | — | — | — |
| Cat. Performance | 155 | 453 | 70 | 56 | 65 |
| Butane Feed | 155–170 | — | — | — | — |
| CCl₄ treatment | 170 | 450 | — | — | — |
| Butane Feed | 170–221 | — | — | — | — |
| Cat. Performance | 221 | 457 | 59 | 54 | 54 |
| Butane Feed | 221–243 | 450 | — | — | — |
| Steam treatment | 243–244 | 450 | — | — | — |
| Butane Feed | 244–269 | 456 | — | — | — |
| Cat. Performance | 269 | 456 | 83 | 57 | 79 |
| Butane Feed | 269–288 | — | — | — | — |
| Temp. Runaway | 288–292 | 521 | — | — | — |
| Butane Feed | 292–294 | 520 | — | — | — |
| Cat. Performance | 294 | 450 | 88 | 51 | 76 |
| Cat. Performance | 294–317 | 450 | — | — | — |
| Cat. Performance | 317 | 449 | 49 | 66 | 55 |
| CCl₄ treatment | 317 | 450 | — | — | — |
| Butane Feed | 317–334 | 449 | — | — | — |
| Butane Feed | 334 | 449 | 56 | 66 | 62 |
| Butane Feed | 334–338 | 450 | — | — | — |
| Steam treatment | 338–340 | 450 | — | — | — |
| Butane Feed | 338–404 | 450 | — | — | — |
| Cat. Performance | 404 | 450 | 81 | 61 | 83 |
| Butane Feed | 404–405 | — | — | — | — |
| Temp. Runaway | 405–409 | 524 | — | — | — |
| Butane Feed | 409–430 | 450 | — | — | — |
| Cat. Performance | 430 | 452 | 86 | 54 | 78 |
| Butane Feed | 430–431 | — | — | — | — |
| CCl₄ treatment | 431 | 450 | — | — | — |
| Steam treatment | 431–433 | 450 | — | — | — |
| Butane Feed | 433–475 | — | — | — | — |
| Cat. Performance | 475 | 450 | 82 | 58 | 80 |
| Butane Feed | 475–476 | — | — | — | — |
| Temp. Runaway | 476–480 | 520 | — | — | — |
| Butane Feed | 480–481 | 452 | — | — | — |
| Cat. Performance | 481 | 452 | 90 | 53 | 81 |
| Butane Feed | 481–500 | 452 | — | — | — |
| Cat. Performance | 500 | 452 | 86 | 55 | 80 |
| Butane Feed | 500–504 | 452 | — | — | — |
| Cat. Performance | 504 | 430 | 78 | 62 | 81 |
| Butane Feed | 504–571 | 450 | — | — | — |
| Cat. Performance | 571 | 450 | 85 | 56 | 80 |
| Butane Feed | 571–575 | 450 | — | — | — |
| CCl₄ treatment | 575 | 450 | — | — | — |
| Butane Feed | 575–595 | 450 | — | — | — |
| Cat. Performance | 595 | 449 | 41 | 68 | 47 |
| Steam treatment | 595–599 | 450 | — | — | — |
| Cat. Performance | 599 | 450 | 79 | 63 | 84 |
| Butane Feed | 599–618 | 450 | — | — | — |
| Cat. Performance | 618 | 451 | 78 | 60 | 80 |
| Butane Feed | 618–620 | 450 | — | — | — |
| Temp. Runaway | 620–624 | 521 | — | — | — |
| Butane Feed | 624–625 | 450 | — | — | — |
| Cat. Per- | | | | | |

TABLE I-continued

| Operation | Time On-Stream, Hrs. | Temperature, °C. | Conversion to MAN, Percent | Selectivity to MAN, Percent | Weight Yield to MAN Percent |
|---|---|---|---|---|---|
| formance | 625 | 451 | 86 | 57 | 82 |
| Butane Feed | 625–643 | 451 | — | — | — |
| Cat. Performance | 643 | 451 | 84 | 58 | 82 |
| Butane Feed | 643–668 | 451 | — | — | — |
| Cat. Performance | 668 | 451 | 82 | 56 | 77 |
| Butane Feed | 668–669 | 451 | — | — | — |
| CCl₄ treatment | 669 | 450 | — | — | — |
| Butane Feed | 669–670 | 448 | — | — | — |
| Cat. Performance | 670 | 448 | 61 | 72 | 75 |
| Butane Feed | 670–671 | 450 | — | — | — |
| Steam treatment | 671–672 | 450 | — | — | — |
| Butane Feed | 672–673 | 450 | — | — | — |
| Cat. Performance | 673 | 450 | 65 | 70 | 77 |
| Butane Feed | 673–764 | 449 | — | — | — |
| Cat. Performance | 764 | 449 | 78 | 58 | 77 |
| Butane feed | 764–843 | 451 | — | — | — |
| Cat. Performance | 843 | 451 | 82 | 58 | 80 |
| Butane Feed | 843–933 | 450 | — | — | — |
| Cat. Performance | 933 | 450 | 81 | 54 | 75 |

EXAMPLE II

In this Example three catalysts having identical compositions to that of Example I were tested. All three of the catalysts had been contacted with a butane-air mixture for about 518 hours to produce maleic anhydride and then regenerated using carbon tetrachloride. The regeneration took place after a ½ hour nitrogen purge over the catalyst. Regeneration conditions included a temperature of 460° C., a concentration of 8 volume percent carbon tetrachloride in nitrogen flowing at a weight hourly space velocity of about 1.4 (based on CCl₄) until a quantity of carbon tetrachloride equal to about 3 weight percent of the catalyst had contacted the catalyst.

After this regeneration all three of the catalysts were subjected to a butane-air feed mixture at reaction conditions essentially the same as described in Example I except that the catalyst was maintained at 460° C. to rapidly degrade the catalyst with occasional excursions (usually 2–3 hours) down to temperatures of 400° C. to measure catalyst performance at the lower temperature.

Catalysts A and B were only regenerated once and the reported selectivities and weight yields in percent are shown for the indicated catalyst life periods. Catalyst C was alternately run for about 518 hours on butane-air then regenerated as described above. This sequence was continued until the catalyst had been regenerated a total of 8 times, the catalyst having about 4142 total hours of operation on the butane-air mixture just prior to the eighth and last regeneration. The reported data for Catalyst C is for the period just after the eighth regeneration.

TABLE II

| Catalyst Description | Time After Last Regeneration, Hours | Selectivity To MAN, % | | Weight Yield, To MAN, % | |
|---|---|---|---|---|---|
| | | 460° C | 400° C | 460° C | 400° C |
| CATALYST A (Regenerated once) | 3 | 48 | — | 79 | — |
| | 20 | 37 | — | 61 | — |
| | 21 | 37 | 60 | 62 | 78 |
| | 112 | 36 | — | 59 | — |
| | 114 | 34 | — | 56 | — |
| | 136 | 34 | — | 57 | — |
| | 181 | 28 | 51 | 48 | 70 |
| | 747 | — | — | — | 56 |
| CATALYST B (Regenerated once) | 19 | 39 | 59 | 63 | 80 |
| | 44 | 36 | — | 60 | — |
| | 69 | 33 | 54 | 54 | 76 |
| | 92 | 33 | — | 53 | — |
| | 160 | 32 | 52 | 52 | 74 |
| | 181 | 29 | 52 | 48 | 74 |
| | 747 | — | — | — | 56 |
| CATALYST C (Regenerated 8 times) | 1 | 55 | — | 89 | — |
| | 18 | 45 | 65 | 73 | 87 |
| | 41 | 41 | — | 67 | — |
| | 67 | 40 | 62 | 65 | 85 |
| | 90 | 38 | — | 63 | — |
| | 158 | 37 | 60 | 61 | 81 |
| | 205 | 35 | 60 | 58 | 83 |
| | 226 | 35 | — | 58 | — |
| | 248 | 35 | 59 | 58 | 82 |
| | 320 | 34 | 58 | 57 | 82 |

The data in Table II above illustrate that the catalyst becomes less sensitive to selectivity and yield declines after it has been subjected to repetitive deactivation and reactivation.

I claim as my invention:

1. A method for stabilizing a phosphorus-vanadium-oxide catalyst having an atomic ratio of phosphorus to vanadium in the range of about 0.5 to 5, which comprises:

(A) Contacting said catalyst at deactivation conditions including a temperature in the range of from about 350° to 600° C. with a gaseous mixture containing molecular oxygen for a period of greater than about 1 hour;

(B) Contacting said catalyst with an effective amount of a material selected from the group consisting of:
  (1) Molecular chlorine or fluorine or mixtures thereof;
  (2) Halides of fluorine, chlorine, bromine or iodine being in the vapor state above about 250° C. at atmospheric pressure represented by the following formula:

$$C(X)_n$$

where each X is a selected halide and $n$ is an integer from 1 to 4, any remaining radicals being hydrogen or mixtures thereof;

(3) Organic halides of fluorine, chlorine, bromine or iodine being in the vapor state above about 250° C. at atmospheric pressure represented by the formula:

$$R(X_1)_m$$

where R is alkane, alkene or alkyne of straight or branched structure having at least two carbon atoms and $X_1$ is independently a primary, secondary, or tertiary halide and m is an integer of from 1 to about 20 consistent with the number of carbon atoms of said structure or mixtures;

(4) hydrogen halides;

or mixtures thereof at reactivation conditions including a temperature in the range of from about 300° to about 500° C.; and (c) repeating the sequence of steps (A) and (B) at least once.

2. The method of claim 1 further characterized in that said gaseous mixture includes a hydrocarbon selected from the group consisting of methane, ethane, propane, n-butane, n-butene or mixtures thereof.

3. The method of claim 2 further characterized in that said hydrocarbon is selected from the group consisting of n-butane and n-butene or mixtures thereof.

4. The method of claim 1 further characterized in that said material of step (B) comprises a meterial represented by the following formula:

$$C(X)_n$$

where each X is independently a halide of chlorine, fluorine or bromine and n is an integer of from 1 to 4, any remaining radicals being hydrogen.

5. The method of claim 1 further characterized in that said material of step (B) is selected from the group consisting of carbon tetrachloride, carbon trichloride, carbon dichloride or methylchloride or mixtures thereof.

6. The method of claim 5 further characterized in that said material of step (B) comprises carbon tetrachloride.

7. The method of claim 1 further characterized in that said deactivation conditions include temperature in the range of from about 380° to 520° C.

8. The method of claim 1 further characterized in that the sequence of steps (A) and (B) is repeated at least three times.

9. A method for stabilizing a phosphorus-vanadium-oxide catalyst having an atomic ratio of phosphorus to vanadium in the range of about 0.5 to 5, which comprises:

(A) Contacting said catalyst at deactivating conditions including a temperature in the range of from about 350° to 600° C. with a gaseous mixture containing molecular oxygen and a hydrocarbon having less than about ten carbon atoms per molecule for a period of greater than about 1 hour.

(B) Contacting said catalyst with an effective amount of a material selected from the group consisting of:

(1) Molecular chlorine or fluorine or mixtures thereof;

(2) Halides of fluorine, chlorine, bromine or iodine being in the vapor state above about 250° C. at atmospheric pressure represented by the following formula:

$$C(X)_n$$

where each X is a selected halide and n is an integer from 1 to 4, any remaining radicals being hydrogen or mixtures thereof;

(3) Organic halides of fluorine, chlorine, bromine or iodine being in the vapor state above about 250° C. at atmospheric pressure represented by the formula:

$$R(X_1)_m$$

where R is alkane, alkene or alkyne of straight or branched structure having at least two carbon atoms and $X_1$ is independently a primary, secondary, or tertiary halide and m is an integer of from 1 to about 20 consistent with the number of carbon atoms of said structure or mixtures;

(4) Hydrochloric acid;

or mixtures thereof at reactivation conditions including a temperature in the range of from about 300° to about 500° C.; and (c) repeating the sequence of steps (A) and (B) at least once.

10. The method of claim 9 further characterized in that said hydrocarbon is selected from the group consisting of methane, ethane, propane, n-butane, n-butene or mixtures thereof.

11. The method of claim 10 further characterized in that said hydrocarbon is selected from the group consisting of n-butane and n-butene or mixtures thereof.

12. The method of claim 9 further characterized in that said material of step (B) comprises a material represented by the following formula:

$$C(X)_n$$

where each X is independently a halide of chlorine, fluorine or bromine and $n$ is an integer of from 1 to 4, any remaining radicals being hydrogen.

13. The method of claim 9 further characterized in that said material of step (B) is selected from the group consisting of carbon tetrachloride, carbon trichloride, carbon dichloride or methylchloride or mixtures thereof.

14. The method of claim 13 further characterized in that said material of step (B) comprises carbon tetrachloride.

15. The method of claim 9 further characterized in that said temperature of step (A) is in the range of from about 380° to 520° C.

16. The method of claim 9 further characterized in that the sequence of steps (A) and (B) is repeated at least three times.

17. A method for stabilizing a phosphorus-vanadium-oxide catalyst having pentavalent phosphorus and vanadium with an average valence in the range of from about 3.9 to about 4.5, an atomic ratio in the range of from about 1 to 2, which comprises:

(A) contacting said catalyst at deactivation conditions including a temperature in the range of about 350° to 540° C. with a gaseous mixture containing molecular oxygen and a hydrocarbon having less than about seven carbon atoms per molecule for a period of greater than about one hour;

(B) contacting said catalyst with an effective amount of a material selected from the group consisting of methyl chloride, carbon dichloride, carbon trichloride, or carbon tetrachloride or mixtures thereof, at reactivation conditions including a temperature in the range of from about 300° to about 500° C;

(C) contacting said catalyst with steam at a temperature in the range of from about 400° to 500° C; and (D) repeating the sequence of steps (A), (B) and (C) at least once.

18. The method of claim 17, step (A) further characterized in that said hydrocarbon comprises normal butane, the temperature is in the range of from about 400° to about 540° C. and the contacting is a period of greater than about three hours.

19. The method of claim 17, step (B) further characterized in that said material comprises carbon tetrachloride and the temperature is in the range of from about 400° to 500° C.

20. The method of claim 17, step (C) further characterized in that said steam contact takes place at a temperature in the range of from about 400° to 500° C.

21. The method of claim 17 further characterized in that: in step (A) the hydrocarbon comprises normal butane, the temperature is in the range of from about 500° to about 540° C. and the contacting is a period of greater than about three hours; in step (B) said material comprises carbon tetrachloride and the temperature is in the range of from about 400° to 500° C; in step (C) said steam contact takes place at a temperature in the range of from about 400° to 500° C; and the sequence of steps (A), (B) and (C) is repeated at least three times.

22. A method for stabilizing a phosphorus-vanadium-oxide catalyst having an atomic ratio of phosphorus to vanadium in the range of from about 0.5 to about 5 and containing an atomic ratio of zinc to vanadium of from about 0.01 to about 0.3 which method comprises:

(A) contacting said catalyst at a temperature above about 370° C. with a gas containing molecular oxygen and a hydrocarbon selected from the group consisting of normal butane, normal butene-1, normal butene-2, butadiene, benzene or mixtures thereof for greater than about one hour;

(B) contacting said catalyst with carbon tetrachloride at a temperature in the range of from about 300° to about 500° C; and (C) repeating the sequence of steps (A) and (B) at least once.

23. The method of claim 22 further characterized in that said step (B) takes place at a temperature in the range of from about 350° to about 450° C.

24. The method of claim 22 further characterized in that the hydrocarbon of step (A) is selected from the group consisting of normal butane, normal butene-1, normal butene-2, butadiene or mixtures thereof and is present at below about 1.7 volume percent of the gas.

25. The method of claim 22 further characterized in that the phosphorus is pentavalent and the vanadium has a valence in the range of from about 4 to about 4.5.

26. The method of claim 22 further characterized in that from about 0.1 to about 10 percent by weight based on active catalyst of carbon tetrachloride contacts the catalyst in each step (B).

27. The method of claim 22 further characterized in that steps (A) and (B) are repeated at least three times.

* * * * *

UNITED STATES PATENT OFFICE

CERTIFICATE OF CORRECTION

Patent No. 4,094,816        Dated June 13, 1978

Inventor(s)  Walter Partenheimer

It is certified that error appears in the above-identified patent and that said Letters Patent are hereby corrected as shown below:

| Patent Column | Line | |
|---|---|---|
| 1 | 57 | "phosphorusvanadium" should read -- phosphorus-vanadium -- |
| 2 | 26 | "produces" should read -- products -- |
| 3 | 11 | "phosphorusvanadium" should read -- phosphorus-vanadium -- |
| 3 | 40 | *"N-butane" should read -- n-butane -- |
| 4 | 68 | "for instance" should read -- For instance -- |
| 6 | 2 | "products(s)" should read -- product(s) -- |
| 9 | 56 | *"catalyst a" should read -- catalyst at a -- |
| 10 | 8 | *"nitrogen steam" should read -- nitrogen stream -- |

UNITED STATES PATENT OFFICE
CERTIFICATE OF CORRECTION

Patent No. 4,094,816  Dated June 13, 1978

Inventor(s) Walter Partenheimer

It is certified that error appears in the above-identified patent and that said Letters Patent are hereby corrected as shown below:

| Patent Column | Line | |
|---|---|---|
| 15 | 33 | "meterial" should read -- material -- |

Signed and Sealed this

Eleventh Day of December 1979

[SEAL]

Attest:

SIDNEY A. DIAMOND

Attesting Officer   Commissioner of Patents and Trademarks